United States Patent
Zander

(10) Patent No.: US 7,311,710 B2
(45) Date of Patent: Dec. 25, 2007

(54) TARGETING DEVICE FOR A LOCKING NAIL

(75) Inventor: Nils Zander, Eckernförde (DE)

(73) Assignee: Stryker Trauma GmbH (DE)

( * ) Notice: Subject to any disclaimer, the term of this patent is extended or adjusted under 35 U.S.C. 154(b) by 627 days.

(21) Appl. No.: 10/627,876

(22) Filed: Jul. 25, 2003

(65) Prior Publication Data

US 2004/0059329 A1    Mar. 25, 2004

(30) Foreign Application Priority Data

Aug. 1, 2002    (DE) .......................... 202 11 806 U

(51) Int. Cl.
*A61B 17/56*    (2006.01)
(52) U.S. Cl. ............................. 606/53; 606/64; 606/96
(58) Field of Classification Search ............ 606/96–98, 606/62, 64, 53
See application file for complete search history.

(56) References Cited

U.S. PATENT DOCUMENTS

| | | | |
|---|---|---|---|
| 4,103,683 A | | 8/1978 | Neufeld |
| 4,465,065 A | * | 8/1984 | Gotfried ........................ 606/65 |
| 4,622,959 A | | 11/1986 | Marcus |
| 4,733,654 A | * | 3/1988 | Marino .......................... 606/64 |
| 4,865,025 A | * | 9/1989 | Buzzi et al. ................... 606/96 |
| 4,911,153 A | * | 3/1990 | Border .......................... 606/98 |
| 4,913,137 A | | 4/1990 | Azer et al. |
| 5,047,034 A | * | 9/1991 | Sohngen ........................ 606/87 |
| 5,234,434 A | * | 8/1993 | Goble et al. ................... 606/96 |
| 5,281,224 A | | 1/1994 | Faccioli et al. |
| 5,334,192 A | | 8/1994 | Behrens |
| 5,354,300 A | | 10/1994 | Goble et al. |
| 5,766,174 A | | 6/1998 | Perry |
| 5,928,235 A | | 7/1999 | Friedl |
| 6,039,739 A | | 3/2000 | Simon |
| 6,126,661 A | | 10/2000 | Faccioli et al. |
| 6,183,477 B1 | * | 2/2001 | Pepper ........................ 606/104 |
| 2002/0058949 A1 | | 5/2002 | Iaia |
| 2005/0222681 A1 | * | 10/2005 | Richley et al. .......... 623/17.11 |

FOREIGN PATENT DOCUMENTS

| | | |
|---|---|---|
| DE | 43 06 724 A1 | 9/1994 |
| DE | 200 19 026 U1 | 5/2002 |
| EP | 948 936 A2 | 10/1999 |
| JP | 2001286480 | 10/2001 |

* cited by examiner

*Primary Examiner*—Eduardo C. Robert
*Assistant Examiner*—James L. Swiger
(74) *Attorney, Agent, or Firm*—Lerner, David, Littenberg, Krumholz & Mentlik, LLP

(57) ABSTRACT

An aiming device for a locking nail has a first portion detachably connectable with the exposed end of the nail. An aiming arm is connected to the first portion, which, in turn, is connected to an accommodation arm portion which runs approximately parallel to the nail. The accommodation portion has at least one transverse bore for receiving a guiding sleeve. The accommodation portion being provided with a locking portion which is movable in relation to the accommodation portion against a spring force, with the transverse bore being approximately aligned towards an opening in the locking portion. The transverse bore and the opening being disposed such that when the locking portion is relaxed an accommodated guiding sleeve is held slightly clamped and the sleeve is freely movable in a position locking upon a movement of the portion against the spring force.

20 Claims, 3 Drawing Sheets

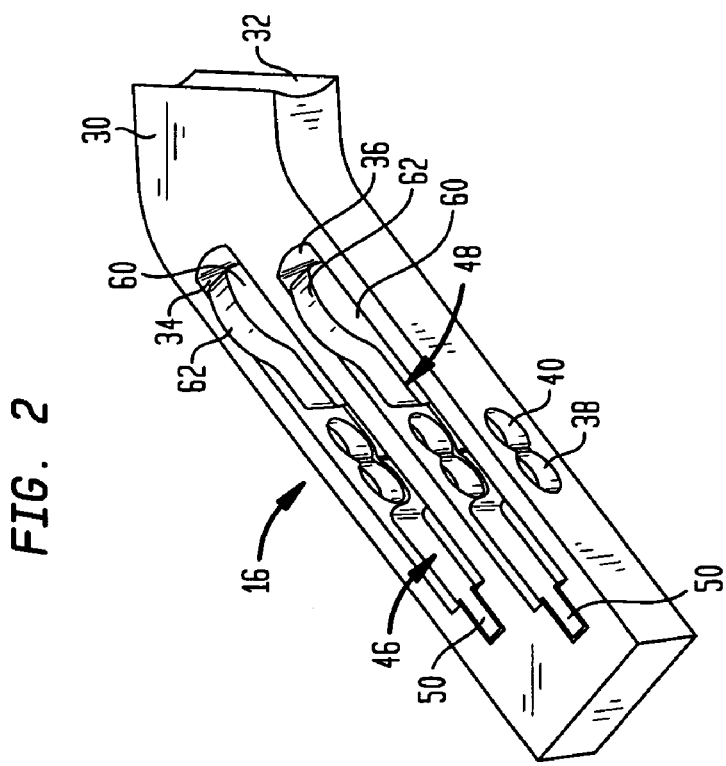
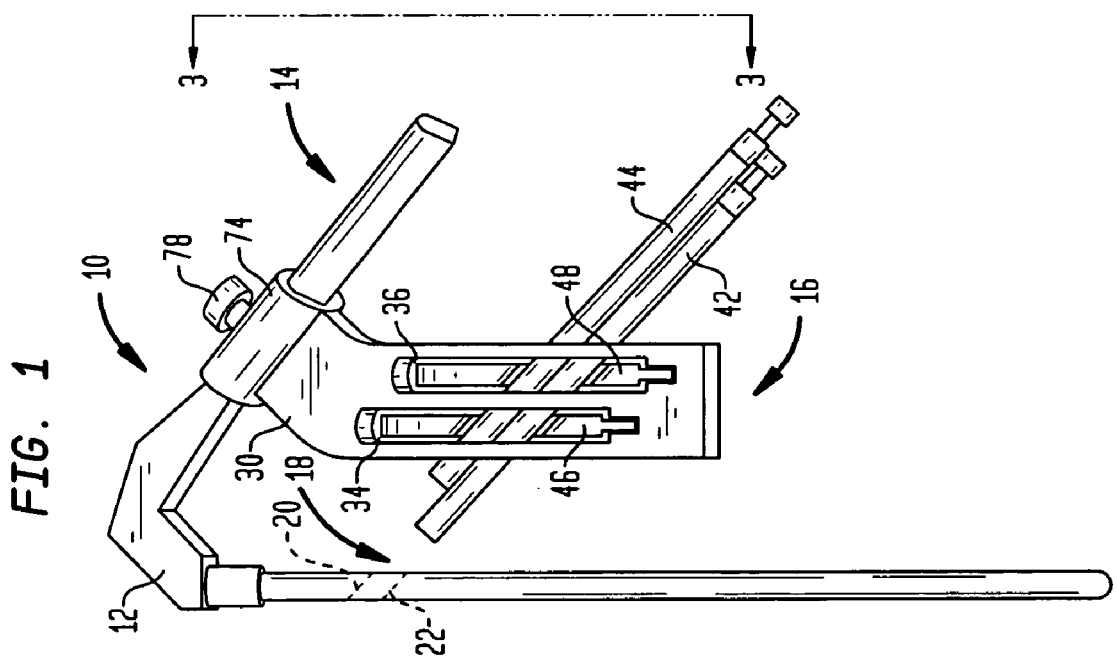

TARGETING DEVICE FOR A LOCKING NAIL

BACKGROUND OF THE INVENTION

The invention relates to an aiming or targeting device for a locking nail or other implant for a long bone. More particularly, the invention relates to a device capable of holding drill guiding sleeves independently on the aiming device.

Locking nails insertable into the tibia or femur bone or other long bones are usually provided with several transverse bores. Bone screws are placed through the bores in order to keep the locking nails securely in the bone channel. A special problem with locking nails is the detection of the transverse bores in the implanted nail. Aiming devices are used for this purpose. One category of aiming devices works with X-rays, and the transverse bores of the locking nail in the bone are imaged on a monitor. Further, a representation of an aiming element aligned with the bores takes place. Thus, it is possible to mark the position on the outer side of the bone which is located on the axis of the transverse bore.

In another category, the aiming devices are fixedly attached to the implanted nail. A bracket-like portion is provided with at least one bore, the axis of which is aligned with the axis of a transverse bore of the nail while it is attached to the aiming device. For the purpose of guiding the drilling tool and the bone screw, respectively, it is also known to put a guiding sleeve through the transverse bore of the aiming device, which sleeve is moved forward until the outer side of the bone is reached.

The guiding sleeve is fittingly seated in the transverse bore of the first arm portion of the aiming device, but has to be moved easily by hand, in order not to complicate the work of the surgeon. Through this, there is the danger that the guiding sleeve slips rearwardly upon handling the aiming device, and upon drilling and also upon screwing in of bone screws, respectively. It has become known from U.S. Pat. No. 6,039,739, the teachings of which are incorporated herein by reference, to form a springy or resilient portion on the first arm portion of the aiming device which has the transverse bore or aiming bore of the aiming device, the resilient portion being provided with a bore which is aligned to the transverse bore. When the resilient portion is relaxed, the sleeve is held slightly clamped and is released when the resilient portion is deflected in the direction of the first arm portion.

For the operative repair of fractures in the femur head and neck region it is known to insert two longer bone screws approximately parallel, which are held by corresponding angled transverse bores of a locking nail. The first arm portion of the aiming device is provided with corresponding angled aiming bores. In order to maintain both guiding sleeves clamped, yet detachable, it is possible to provide the resilient portion of the known aiming device with two transverse passages. In this design, however, it is necessary that the two sleeves always must be clamped or released only at the same time.

SUMMARY OF THE INVENTION

The invention has as one objective to create an aiming device for a locking nail, in which two guiding sleeves can be adjusted and fixed in the respective position in a simple manner. Particularly, an independent adjustability and positioning of two parallel guiding sleeves shall be made possible.

These and other objects of the invention are accomplished by an aiming device for a locking nail which has a connecting portion connectable to an end of the locking nail and having an aiming arm with a first portion which extends generally parallel to the nail when the nail is implanted and the connecting portion is connected to the end of the nail. The first portion is provided with at least one and preferably two transverse bores extending along an axis, each bore for receiving a guiding sleeve. The first portion has at least one slot therein intersecting the bore, which slot contains a biased lever or locking element having a first end attached to a first end of the slot. The lever or locking element has a second end having a sleeve contacting surface. The lever or locking element is biased against the sleeve. The slot and the lever or locking element are disposed such that the lever or locking element may be swiveled or moved out of contact with the guiding sleeves. This may be done by including a curved portion extending beyond the plane of the slot, which portion may be moved by hand against the biasing force to release the pressure on this sleeve and allow the repositioning thereof. Generally, this movement is in a plane which is generally perpendicular to the axis of the transverse bore and out of engagement with the sleeve.

The lever or locking element is designed to engage only one of the two sleeves and thus, to lock both sleeves, two levers or locking elements are provided in the first portion of the aiming arm. This allows each sleeve to be independently released by movement of the lever of the locking element out of engagement therewith.

In one embodiment, resilient levers or locking elements are placed in parallel slots in the first portion. The sleeve contacting surface of the lever or locking element is provided with two adjacent openings or recesses and the openings or recesses of each lever are formed to contact only one of the two sleeves respectively. The lever may be made of a resilient material having a first end portion received at and attached to one end of the slot. This attachment to the slot may be by a portion having a relatively small in cross-section when compared to the second end or sleeve contacting portion of the lever. This smaller cross-section may be fixed in the slot in the first portion by gluing, riveting, pinning or clamping. The first portion can be movably mounted on the aiming arm and capable of being fixed at a selected location, usually in the longitudinal direction thereon. The first portion may be provided with an angled connecting portion which connects with a second portion of the aiming arm which runs at an acute angle with respect to the longitudinal axis of the implanted nail. The angled connecting portion ensures that the first portion extends generally parallel to the nail axis.

The first portion and/or the levers or locking elements are formed from a carbon fiber reinforced plastic material. Alternately, the levers may be made from a hard rubber. The hard rubber or plastic levers or locking elements are aligned so that when the sleeves are not present within the bores of the first portion of the aiming arm, they overlap the bores. Thus, when the sleeves are inserted, the levers or locking elements must be deflected out of the path of the bores and thus, when released, spring back and are prevented from their fully relaxed position by contact with the guide sleeves. It can be seen that the levers or locking elements can be made out of a non-resilient material with a metal spring, such as a leaf spring, mounted on the first portion of the aiming arm to move the non-resilient levers or locking elements against the guide sleeves and maintain them in position during use. The first portion of the aiming arm may be non-rotatably mounted on the second portion but may be moved axially therealong and locked into position by a locking screw.

In the preferred aiming device of the present invention, the first portion of the aiming device is provided with an oblong slot, which extends into the longitudinal direction of the first arm portion, this extension being transverse to the bores in the first arm portion. In the slot, a lever preferably made from elastically yielding material is attached by fixing an end region of the lever to one end of the slot. The other end region of the lever is provided with a handle or a protrusion sticking out from the slot. The slot and lever are disposed such that upon operation of the handle, the lever is swiveled in a plane which is perpendicular to the transverse bore of the first arm portion. In the lever, a recess or opening is formed, through which the guiding sleeve can extend, an accommodated sleeve being clamped therein. However, the recess or opening of the lever being located somewhat eccentric when the lever is in the relaxed condition. If the lever is slightly swiveled, however, an alignment of the recess or openings which the transverse bore takes place, and the guiding sleeve is easily movable into the desired direction.

The inventive solution is particularly advantageous when there are two angled transverse bores in the accommodation portion which are situated relatively closely to each other. Upon implantation of a bone nail as carrier for two parallel bone screws for the operative repair of fractures in the femur neck and head region. For this purpose, the first arm portion is provided with two angled transverse bores, situated closely to each other. The first arm portion is provided with two parallel slits, each of which accommodates one lever. Each lever has a first end provided with adjacent openings or recesses, and the openings or recesses are formed such that parallel sleeves are individually and separately, independent from each other, held clamped in position but are detachable. Thus, the operation of one lever for the displacement of one guiding sleeve does not result in detachment of the other sleeve, but rather the latter remains situated in its position. Additionally, the invention makes possible the bringing of the two bone screws extraordinarily close together. As is generally known, the diameter of the femoral neck predetermines the maximal distance between the two bone screws which are to be inserted.

The lever can be formed such that it is elastically deformable in itself, comparable to a bending bar clamped in at one end. According to one embodiment of the invention, it is provided that a second end portion of the lever is accommodated in and fixed in a recessed portion of the slot, for instance by gluing. The second end portion is connected with the first part of the lever via a connecting portion of relatively small cross-section. Thus, the deformation upon operation of the lever takes place essentially in the connection portion. Any deformation of the recess or opening upon operation of the lever does not take place in this case.

According to a further embodiment of the invention, the first arm portion is movable, but may be fixed on the aiming arm in a desired position. According to a form of the invention, the second aiming arm portion extends at an acute angle with respect to the axis on which the nail which is fixed on the aiming arm is situated, and the first arm portion is provided with an annexation or connection portion offset at an obtuse angle, which is movably guided on the second aiming arm portion. The second aiming arm portion and the annexation portion are formed such that the first portion extends approximately parallel to the nail axis.

Preferably, the accommodation portion and/or the levers are formed from carbon fiber reinforced plastic material such as PEEK (polyetheretherketone). This material provides a sufficient stability for an aiming device, but has the advantage to be transparent for X-rays.

BRIEF DESCRIPTION OF THE DRAWINGS

An example of the invention will be explained in more detail below by means of drawings.

FIG. 1 shows, in perspective, an aiming device according to the invention with an accommodated bone nail;

FIG. 2 shows in perspective the first arm portion of the aiming device according to FIG. 1;

DETAILED DESCRIPTION

Figure 3:
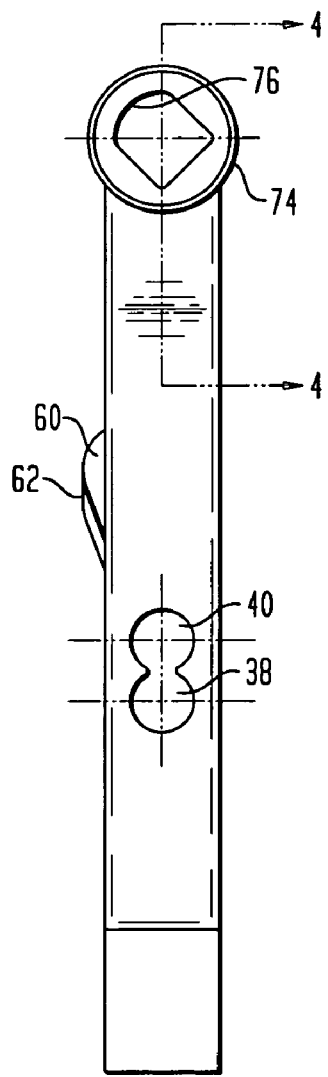
FIG. 3 shows the lateral view of the first arm portion of the aiming device according to FIG. 1, in direction of arrow 3.

Referring to FIG. 1 there is shown an aiming device 10, which is provided with a nail connecting portion 12 on which is slidably mounted on a first aiming arm portion 16. A second portion 14 is also attached to portion 12. In the preferred embodiment, second aiming arm portion 14 is one piece and integral with portion 12. First arm portion 16 is axially movably disposed on the second aiming arm portion 14. A locking nail 18 is fixed on portion 12. Locking nail 18 is provided with two angled transverse bores, which are denoted by their axis 20 and 22. The locking nail 18 is also provided with transverse bores in the distal region, which are not shown, however. Locking nail 18 serves for the accommodation of two parallel bone screws situated closely together, for the operative repair of a fracture in the region of the femur head or neck.

Figure 6:
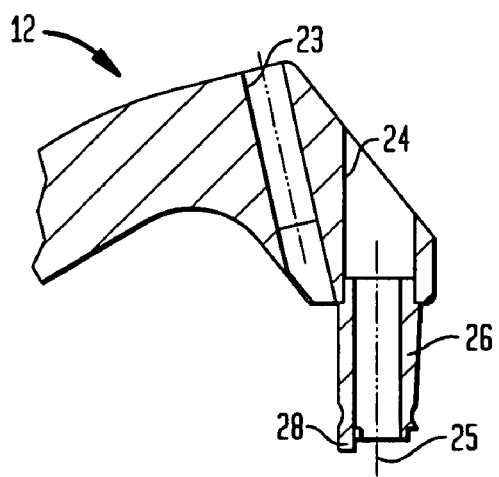
FIG. 6 shows a section through a part of the second aiming arm portion of the aiming device according to FIG. 1, in the region of the connection site with the nail.

As can be recognized from FIG. 6, portion 12 is provided with an accommodation bore 24 for a sleeve 26, which cooperates with the end of nail 18. Sleeve 26 has on the bottom free end a projection 28 parallel to axis 25 which cooperates with a recess in nail 18 (not shown) in order to determine the angle position of the nail. A fixing bolt is guided through bores 24 and sleeve 26 for attaching a threaded end of nail 18 on aiming device 10 (not shown in detail). A threaded bore 23 serves for the attachment of a stop or the like, by which the aiming device, and also nail 18, can be driven via a knocking instrument such as a hammer.

In the preferred embodiment, the construction of first arm portion 16 is shown in more detail in FIGS. 2, 3, 4 and 5. It can be seen that portion 16 constitutes an oblong body rectangular in its cross-section, which on one end has a connection portion 30 offset with respect to the main body at an obtuse angle, which on the free end has in cross-section a curved circular arc-shaped recess 32. Preferably, the first portion 16 has two parallel slots 34, 36 which extend completely through portion 16. As can be seen from FIG. 1, slots 34, 36 extend into a plane which is parallel to the axis of nail 18. First arm portion 16 also extends parallel to the nail axis.

In the preferred embodiment, two parallel angled bores 38, 40 extend through the individual bridges of first arm portion 16, which are formed by slots 34, 36. In the preferred embodiment, bores 38, 40 are located so closely together that the wall of bores 38, 40 intersect and is open in the adjoining region. Bores 38, 40 serve for the accommodation of guiding sleeves 42, 44 (FIG. 1), which can be brought together very closely in this manner. The guiding sleeves have the known function to guide tools such as bone drills upon insertion of bone nails or to guide bone nails upon their implantation, respectively, after bores have been formed in the cortical substance of the bone in a known manner. For the rest, reference is made to the description of an aiming device with comparable construction according to U.S. Pat. No. 6,039,739.

Figure 7:
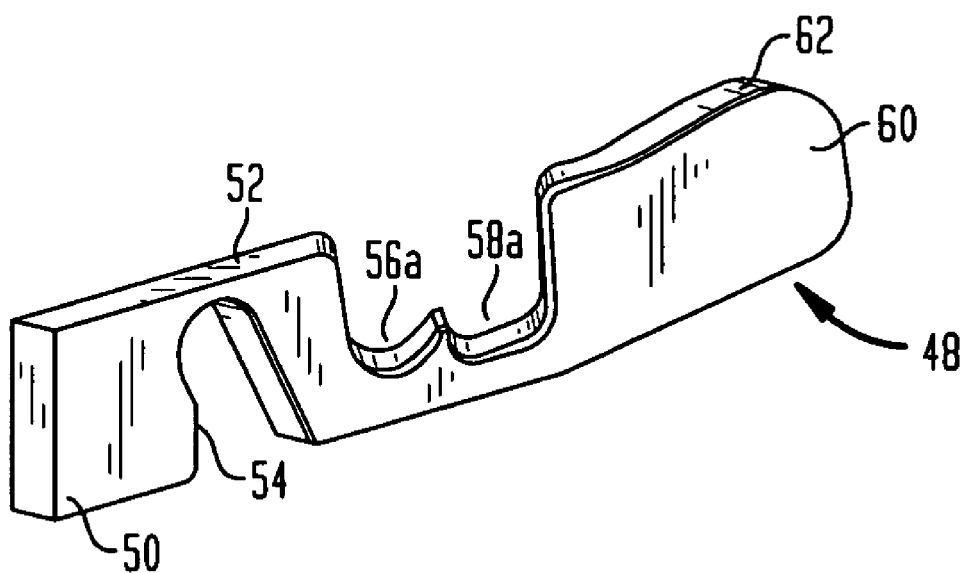
FIG. 7 shows a lever from the right slot of the first portion according to FIG. 2.
Figure 8:
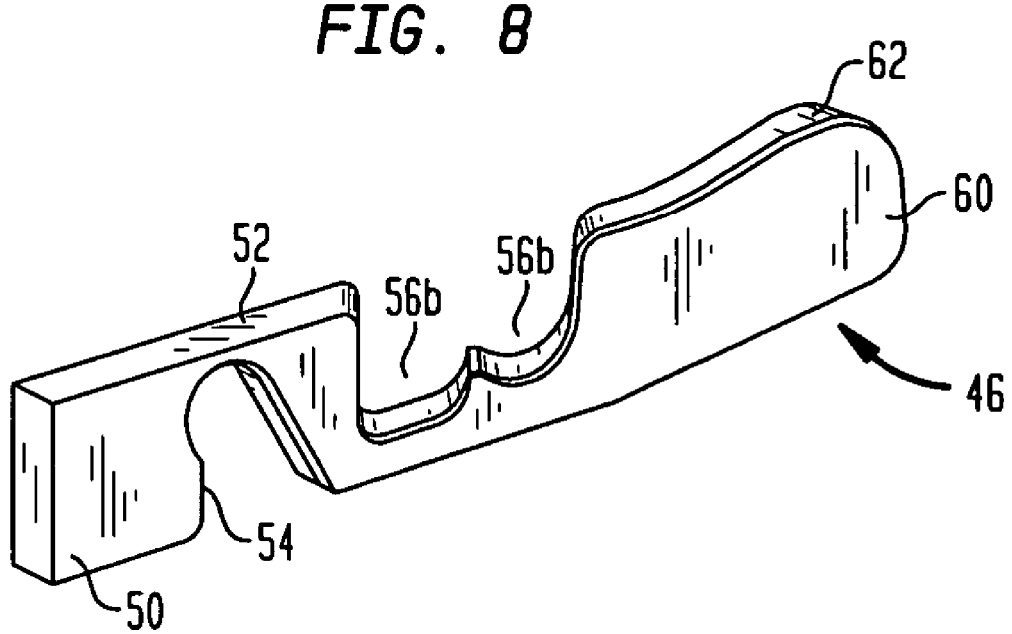
FIG. 8 shows the lever from the left slot of the first portion according to FIG. 2.

In the preferred embodiment, levers 46, 48 are disposed in slots 34, 36. The construction of levers 46, 48 is disclosed in FIGS. 7 and 8. Levers 46, 48 are constructed in an approximately identical fashion and are preferably made of a resiliently deflectable material. For this reason, similar parts shall be provided with the same members. In the preferred embodiment, levers 46, 48 are provided with a first end portion 50, which is disposed in a narrower end region of slots 34, 36, as can be seen in FIG. 2, and which is fixed therein by gluing. An additional or alternate attachment can occur with the aid of pins (not shown). As shown in FIGS. 7 and 8, end portion 50 is followed by an upper annexation portion 52 of relatively small thickness, which is formed as a base of a transverse recess 54 which is formed in lever 46, 48. In the central region of the levers 46, 48 recesses 56a, 58a and 56b, 58b are situated, respectively. Towards the right in the figures, a handle or production 60 follows which is provided with a curved portion 62 projecting somewhat upward. In the assembled condition, curved portion 62 extends somewhat above the associated plane of the preferred first arm portion 16 (see FIGS. 2 and 3). Now, the recesses 56a, 58a and 56b, 58b are formed such that a guiding sleeve 42, 44, which is guided through the transverse bore 38, cooperates with the lever 48 in a clamping manner when the latter is in the relaxed or released condition. A sleeve, which is guided through the transverse bore 40, is clamped fast by recess 58b of the lever 46, when this lever is in the relaxed condition. Thus, each sleeve is clamped by one lever, respectively, when the levers are in the relaxed condition. When one of the levers 46, 48 is slightly deflected in the direction into the slot by pressing on the portion 62, the sleeve which is clamped by this lever is released, so that is can be moved. Thus, sleeves 42, 44 can be moved and be held in their position independently from each other.

Figure 4:
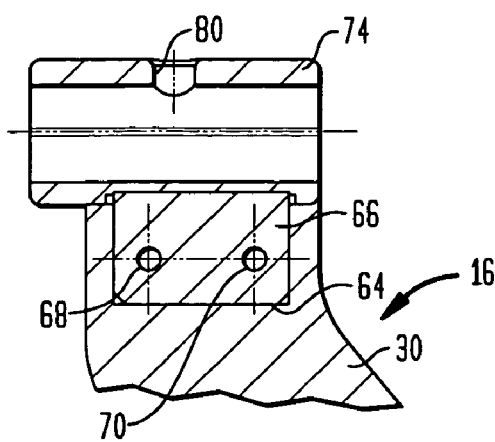
FIG. 4 shows a section through the representation according to FIG. 3 along the line 4-4.
Figure 5:
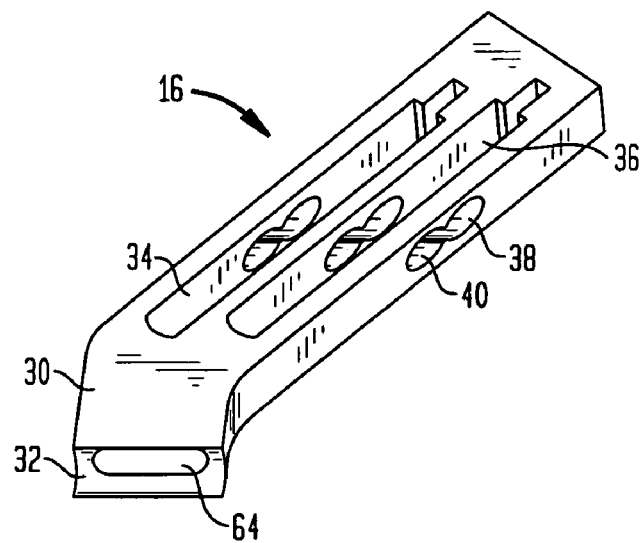
FIG. 5 shows a further perspective view of the first arm portion of the aiming device according to FIG. 1, without accommodated levers.

As shown in FIGS. 4 and 5 in the preferred embodiment, angled annexation or connecting portion 30 has on its free end a recess 64. Recess 64 serves for the accommodation of a connecting piece 66 in the form of a metal insert plate, which is held in the recess 64 by two pins 68, 70 and optionally also by gluing. The metal insert 66 projects somewhat from the bottom of the curved recess 32. A metal guiding sleeve 74, preferably made of stainless steel, has a passage with a noncircular cross-section, as can be seen in FIG. 3. The cross-sectional profile of the second aiming arm portion 14 is complementary to the cross-section of passage 76 of sleeve 74. Sleeve 74, which preferably has a circular outer perimeter, is fitted into fillet 32 and glued fast there. An outer recess of sleeve 74 cooperates with the projecting part of the metal plate 66, by which the sleeve is additionally held onto first arm portion 16 in an effective manner. Thus, with the aid of the sleeve, the accommodation portion can be moved along the second aiming arm portion 14, any rotation, however, being prevented.

Locking screw 78 is screwed into a hole 80 of the sleeve 74, and serves to fix first portion 16 on aiming arm 14.

In the preferred embodiment, accommodation portion 16 is formed from carbon-fiber reinforced plastic material such as, for example, PEEK (polyetheretherketone) as well as are levers 46, 48. Thus, they are transparent for X-rays. The remaining parts are from corrosion-free steel.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An aiming device for a locking nail comprising a connecting portion, connectable to an end of the nail and having an aiming arm with a first portion which extends approximately parallel to the nail when the nail is connected with the connecting portion, the first portion is provided with at least one transverse bore extending along an axis having a guiding sleeve, wherein said guiding sleeve has a longitudinal axis and said first portion has at least one slot intersecting said bore, a lever moveably mounted within the slot and having a first end attached to a first end of the slot and having a second region, said lever second region having a sleeve contacting surface in the form of a recess having an open portion for receiving an outer surface of said sleeve, said open portion open in a direction generally perpendicular to the longitudinal axis of said sleeve, a means for biasing the recess in the lever against the sleeve, the slot and the lever being disposed such that the lever may be moved against the action of the biasing means in a plane which is generally perpendicular to the axis of the sleeve and out of engagement with an outer surface of said sleeve.

2. The aiming device as set forth in claim 1 wherein the nail and the first portion are provided with two angled bores closely spaced together, each for receiving a guide sleeve, the first portion is provided with two parallel slots accommodating a lever, the sleeve contacting surface of each lever is provided with two adjacent recesses each recess having a different depth with the shallower recess adapted to contact the outer surface of one of said two sleeves.

3. The aiming device as set forth in claim 1 wherein the first end portion of the lever is fixedly attached to the first end of the slot has a smaller cross-section than the second end region of the lever.

4. The aiming device as set forth in claim 3 wherein the end portion of the lever is fixed in the slot by gluing.

5. The aiming device as set forth in claim 1 wherein the first portion is movable on an aiming arm and capable of being fixed at a selected location thereon.

6. The aiming device as set forth in claim 5 wherein the first portion is provided with a connecting portion offset with an obtuse angle, and the aiming arm runs in an acute angle with respect to a longitudinal axis of an implanted nail such that the first portion extends approximately parallel to the nail axis.

7. The aiming device as set forth in claim 1 wherein the first portion and/or the levers are formed from carbon fiber reinforced plastic material.

8. The aiming device as set forth in claim 6 wherein the first portion is connected to a sleeve portion which is moveable in a non-rotatable manner on the aiming arm.

9. An aiming apparatus for locating an implant in a long bone, the implant having at least two transverse bores therethrough, the apparatus comprising:

an aiming arm connected to the implant, the arm having a first portion for extending adjacent a long bone and having at least two bores alignable with the at least two bores in the implant;

at least two guide sleeves each having a generally cylindrical bore extending along a central axis of the guide sleeve, one guide sleeve mounted in each bore in the first portion of the aiming arm; and a selectively movable means mounted in a slot in the first arm portion independently engaging and holding said one sleeve mounted in each of said aiming arm bores, said means allowing the selective independent engagement of each sleeve in said bores by movement of said selectively moveable means in direction generally perpendicular to said guide sleeve bore central axis.

10. The aiming apparatus as set forth in claim 9 wherein the means for holding said sleeve in each of said aiming arm bores comprises a separate biased lever associated with said sleeve in each bore, each separate lever mounted in a slot on said first portion, each separate lever biased into engagement with only a respective one of said sleeves.

11. The aiming apparatus as set forth in claim 9 wherein said sleeve in each bore has a separate biased lever engageable therewith, each biased lever having a recess for accommodating said respective sleeve in each bore with only a single recess having a surface contacting a respective one of said sleeves in each bore.

12. The aiming apparatus as set forth in claim 11 wherein the separate lever is made of a resiliently deflectable material and is mounted in a slot in said first portion, each lever having a first end fixed at a first end of said slot and having a handle at a second end for resiliently deflecting the lever about their fixed ends out of engagement with said respective sleeve in each bore.

13. An aiming apparatus for locating bores in a device implanted in a long bone comprising:

an aiming arm connected to the implanted device and having a first portion adapted to extend generally parallel to a longitudinal axis of a long bone, the first portion having two bores therethrough extending in a direction not parallel to the longitudinal axis;

first and second guide sleeves respectively associated with each aiming arm bore having a generally cylindrical outer surface mounted in each of said aiming arm bores such that a central axis of the first and second guide sleeve and the respective aiming bore axis are concentric; and first and second resilient locking elements moveably mounted on said first portion, means for biasing each locking element in a direction generally perpendicular to the guide sleeve central axis towards the outer surface of the first and second guide sleeves, each locking element having an open recess defining a surface engageable with an outer surface of only a single one of said first and second sleeves by movement in the direction perpendicular to the guide sleeve bore axis by the biasing means.

14. The aiming apparatus as set forth in claim 13 wherein the nail and the first portion are provided with two angled bores closely spaced together, each for receiving one of said first and second guide sleeves, the first portion is provided with two parallel slots, each for accommodating the first or second a locking elements, the sleeve contacting surface of the first and second locking elements is provided with two adjacent recesses, each recess having a different depth with the shallower recess adapted to contact the outer surface of the first guide sleeve and the deeper recess spaced from the outer sleeve surface of the second sleeve, the shallower recess of the second locking element adapted to contact the outer surface of the second guide sleeve and the deeper recess spaced from the outer surface of the first guide sleeve.

15. The aiming apparatus as set forth in claim 14 wherein a first end of the locking element is fixedly attached to a first end of the slot, said first end of the locking element having a relatively small cross-section compared to a second end portion of the locking element.

16. The aiming apparatus as set forth in claim 15 wherein the first end portion of the locking element is fixed in the slot first end by gluing.

17. The aiming apparatus as set forth in claim 13 wherein the aiming arm is moveable on a connecting portion attached to the device and is capable of being fixed at a selected location thereon.

18. The aiming apparatus as set forth in claim 17 wherein the connecting portion is offset at an angle to a longitudinal axis of an implanted nail such that the aiming arm extends approximately parallel to the nail axis.

19. The aiming apparatus as set forth in claim 13 wherein the aiming arm is connected to a sleeve portion which is moveable in a non-rotatable manner on the connecting portion.

20. The aiming apparatus as set forth in claim 13 wherein the aiming arm and/or the locking elements are formed from carbon fiber reinforced plastic material.

* * * * *

UNITED STATES PATENT AND TRADEMARK OFFICE
CERTIFICATE OF CORRECTION

PATENT NO. : 7,311,710 B2
APPLICATION NO. : 10/627876
DATED : December 25, 2007
INVENTOR(S) : Nils Zander It is certified that error appears in the above-identified patent and that said Letters Patent is hereby corrected as shown below:

Column 2, line 39, after small, delete "in".
Column 2, line 60, "prevented from" should read --prevented from attaining--.
Column 3, line 21, "which" should read --with--.
Column 3, line 27, "implantation of a bone nail" should read --implantation, a bone nail acts--.
Column 3, line 36, after but, delete "are".
Column 4, line 4, "but has the" should read --and has the--.
Column 4, line 34, after connecting portion 12, delete "on".
Column 4, line 42, "axis" should read --axes--.
Column 5, Line 6, "are formed" should read --is formed--.
Column 5, line 51, "that is can" should read --that it can--.
Column 6, line 12, "are from" should read --are made from--.
Column 6, line 54, "lever is fixedly" should read --lever which is fixedly--.
Column 7, line 23, "in direction" should read --in a direction--.
Column 8, line 19, "second a locking elements," should read --second locking elements,--.

Signed and Sealed this

Thirteenth Day of January, 2009

JON W. DUDAS
*Director of the United States Patent and Trademark Office*